(12) United States Patent
Tadigadapa et al.

(10) Patent No.: US 6,935,010 B2
(45) Date of Patent: Aug. 30, 2005

(54) METHOD OF FABRICATING A MICROMACHINED TUBE FOR FLUID FLOW

(75) Inventors: Srinivas Tadigadapa, State College, PA (US); Chialun Tsai, Thousand Oaks, CA (US); Yafan Zhang, Ann Arbor, MI (US); Nader Najafi, Ann Arbor, MI (US)

(73) Assignee: Integrated Sensing Systems, Inc., Ypsilanti, MI (US)

(*) Notice: Subject to any disclaimer, the term of this patent is extended or adjusted under 35 U.S.C. 154(b) by 77 days.

(21) Appl. No.: 10/233,980

(22) Filed: Sep. 3, 2002

(65) Prior Publication Data
US 2003/0061889 A1 Apr. 3, 2003

Related U.S. Application Data

(62) Division of application No. 09/468,628, filed on Dec. 21, 1999, now Pat. No. 6,477,901.

(51) Int. Cl.[7] .............................................. H01S 4/00
(52) U.S. Cl. ........................................................ 29/592.1
(58) Field of Search .................. 29/595, 424, 890.1, 29/25.35, 592.1, 603.07, 603.18; 156/598, 153, 295, 644

(56) References Cited

U.S. PATENT DOCUMENTS

| | | | | |
|---|---|---|---|---|
| 5,027,499 A | * | 7/1991 | Prohaska | ..................... 29/595 |
| 5,435,060 A | * | 7/1995 | Hayes et al. | ................ 29/890.1 |
| 5,568,013 A | * | 10/1996 | Then et al. | .................. 313/532 |
| 5,569,355 A | * | 10/1996 | Then et al. | .................... 438/20 |
| 5,779,837 A | * | 7/1998 | Harvey | ........................ 156/153 |

* cited by examiner

Primary Examiner—Edward Lefkowitz
Assistant Examiner—Jewel V. Thompson
(74) Attorney, Agent, or Firm—Gary M. Hartman; Domenica N.S. Hartman; Hartman and Hartman

(57) ABSTRACT

Micromachine fluidic apparatus incorporates a free-standing tube section and electrodes to actuate or control the movement of the tube section, or to sense the movement of the tube section, or both. Electronic circuitry, which may be disposed on the same substrate as the fluidic portion of the apparatus, is used in conjunction with the tube and electrodes in conjunction with a variety of different applications, including fluid flow measurement, fluid density measurement, fluid viscosity measurement, fluid transport, separation and/or mixing. According to a particular embodiment, the free-standing section of the tube is resonated for fluid flow and density measurements according to the Coriolis effect. Capacitive/electrostatic actuation techniques are used to control or resonate the free-standing section of the tube, and to detect variations in tube movement. Different methods of fabricating micromachine fluidic apparatus are also disclosed, including the use of fusion bonding of non-conducting substrates, high-aspect ratio etching techniques, and anisotropic etching and refill techniques, preferably utilizing chevron-shaped slit openings to fabricate microtube sections.

19 Claims, 9 Drawing Sheets

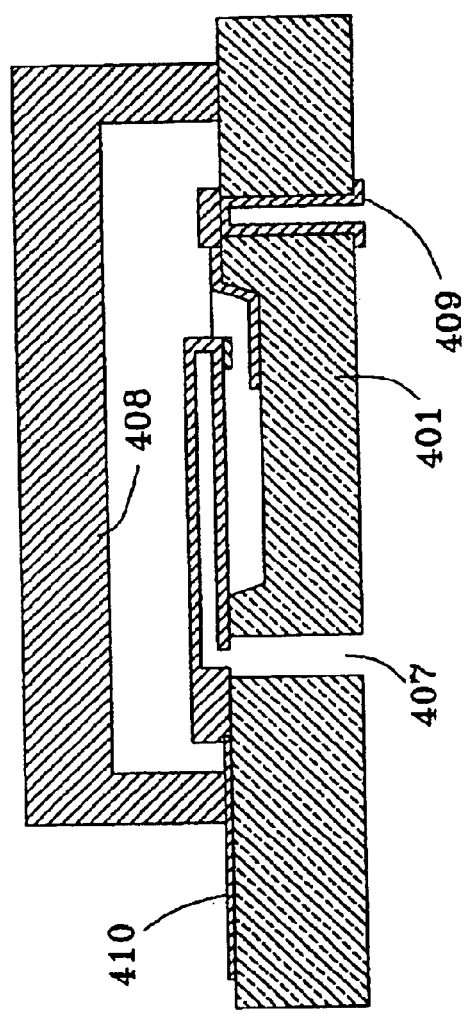
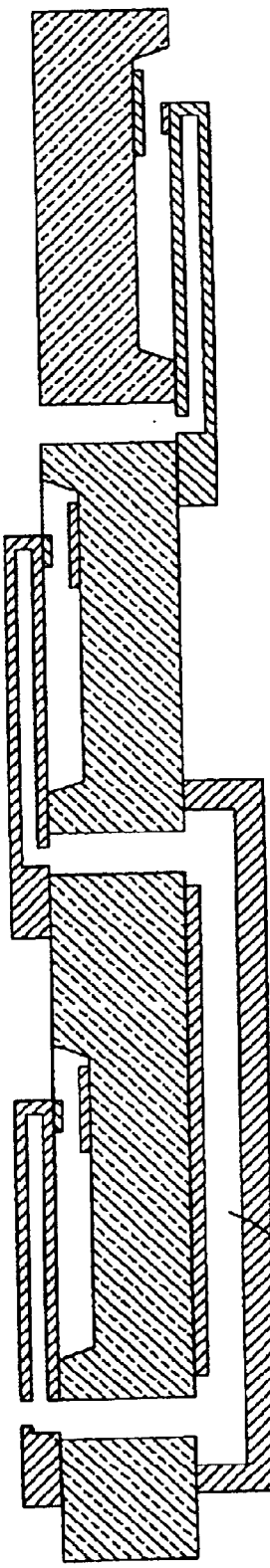
FIG.4
FIG.5

METHOD OF FABRICATING A MICROMACHINED TUBE FOR FLUID FLOW

This is a divisional of application Ser. No. 09/468,628, filed Dec. 21, 1999, now U.S. Pat. No. 6,477,901.

This invention was made with U.S. Government support under SBIR Contract PAN RTW M4-97 awarded by the U.S. Army. The U.S. Government has certain rights in this invention.

FIELD OF THE INVENTION

This invention relates generally to micro-machined fluidic devices, including micro-fluidic apparatus, flow sensors, flow tubes, fluidic density sensors, flow controllers, chemical and biochemical systems, and the like, and, in particular, to the fabrication and implementation of flow measurement devices, fluid density measurement devices and fluidic circuits using silicon microfabrication and precision micromachining techniques.

BACKGROUND OF THE INVENTION

Fluid measurement, control and manipulation are very important in many applications. Direct, accurate on-line measurement of mass flow and fluid density has been made possible through the development of different types of direct mass flow meters. One simple but effective device of this kind is known as the gyroscopic mass flow meter, which takes advantage of the Coriolis force in making measurements.

Since there is but one way of generating Coriolis forces, all existing devices based on gyroscopic or Coriolis force utilize the same basic principles, but specify different means for measuring the force. A number of approaches have been taken in utilizing Coriolis forces to measure mass flow. For instance, Roth, U.S. Pat. Nos. 2,865,201, 3,276,257, and 3,312,512, disclose gyroscopic flow meters employing a full loop, which is continuously rotated (DC type) or oscillated (AC type). The first commercial Coriolis mass flowmeter was introduced in 1977 by Micro Motion Inc. (Boulder, Colo), a member of Rosemount Instrumentation and Control Group. U.S. Pat. No. 4,109,524 teaches the basic principle of this sensor and its construction. Such direct mass flow meters were the first to provide direct, accurate, on-line measurement of mass flow and fluid density. Their major advantages are direct mass flow and fluid density measurements, good accuracy, and high stability. Their major shortcomings are large size and high cost.

Developments in microfabrication techniques and silicon micromachining technology have made it possible to make precision structures for fluidic applications. Silicon as a micromechanical material has been discussed in many papers (J. B. Agnell et. al., 1983, K. E. Bean, 1978, K. E. Petersen, 1982). J. Chen and K. D. Wise have described the methods of making micromachined tubes and channels in silicon. In addition, Peter Enokssen et al. has reported bulk micromachined resonant silicon tube density sensors and mass flow sensors using optical techniques. The need remains, however, to exploit silicon microfabrication techniques to a greater extent in fabricating fluidic apparatus, including direct mass flow meters. It would be particularly advantageous to apply silicon microtubes and other technology to the development of gyroscopic mass flow meters based upon the Coriolis effect.

SUMMARY OF THE INVENTION

This invention broadly relates to micromachined fluidic apparatus. Generally speaking, such apparatus comprises a micromachined tube on or within a substrate, wherein a portion of the length of the tube is free-standing relative to a surface of the substrate, enabling at least the free-standing section to move, twist, vibrate or otherwise deform. One or more electrodes associated with the free-standing section of the tube, in conjunction with one or more electrodes on an opposed, facing portion of the substrate, are used to actuate or control the movement of the free-standing tube section relative to the substrate, or to sense the movement of the free-standing tube section, or both. Electronic circuitry, which may be disposed on the same substrate as the fluidic circuit, is operated with respect to a variety of applications, including fluid flow measurement, fluid density measurement, fluid viscosity measurement, as well as fluid transport, separation and mixing.

Although various techniques may be used to actuate and sense tube movements, capacitive or electrostatic actuation techniques are used to control or resonate the tube, and to detect variations in tube movement for different applications. The capacitive technique is preferred, since the electrodes may be fabricated in the form of capacitor plates integrated to the overall apparatus, with one plate being disposed on the micromachined free-standing tube section, and the other plate being disposed in facing relation on the substrate. According to a specific preferred embodiment, the free-standing section of the tube is resonated for fluid flow and density measurements. A first set of electrodes are used to actuate tube vibration, and adjoining sets of electrodes are used on either side of the actuation electrodes in the corners of a U-shaped tube to facilitate measurements based upon the Coriolis affect, which are described in detail.

Three preferred methods of fabricating micromachined fluidic apparatus for the detection of fluid flow, density and viscosity are also disclosed. The first preferred method utilizes selective etching, boron-doped silicon and silicon fusing bonding to achieve a free-standing micromachined tube section on an insulating substrate. A second preferred method utilizes a buried silicon dioxide layer or doped silicon layers, to create etch stops, with high aspect ratio etching techniques and silicon fusing bonding being used to create a free-standing micromachined tube system, also on a non-conducting substrate. The third preferred method of fabrication takes advantage of the anisotropic etching of silicon, and selective etching, using boron-doped silicon and refill techniques. According to this embodiment, the microtubes are created with respect to a silicon substrate using a boron-doped top layer having chevron-shaped slit-like openings, with anisotropic etching of the underlying undoped silicon being used, followed by boron doping of the tube side-walls and bottom. As a final step, the chevron-shaped openings are refilled to create sealed microtubes.

BRIEF DESCRIPTION OF THE DRAWINGS

FIG. 4 is a cross-section of a micromachined fluidic apparatus having a packaging cap;

FIG. 5 is a cross-section of a fluidic apparatus with micromachined tube systems on both the front and back surfaces of a substrate;

DETAILED DESCRIPTION OF THE INVENTION

Figure 1:
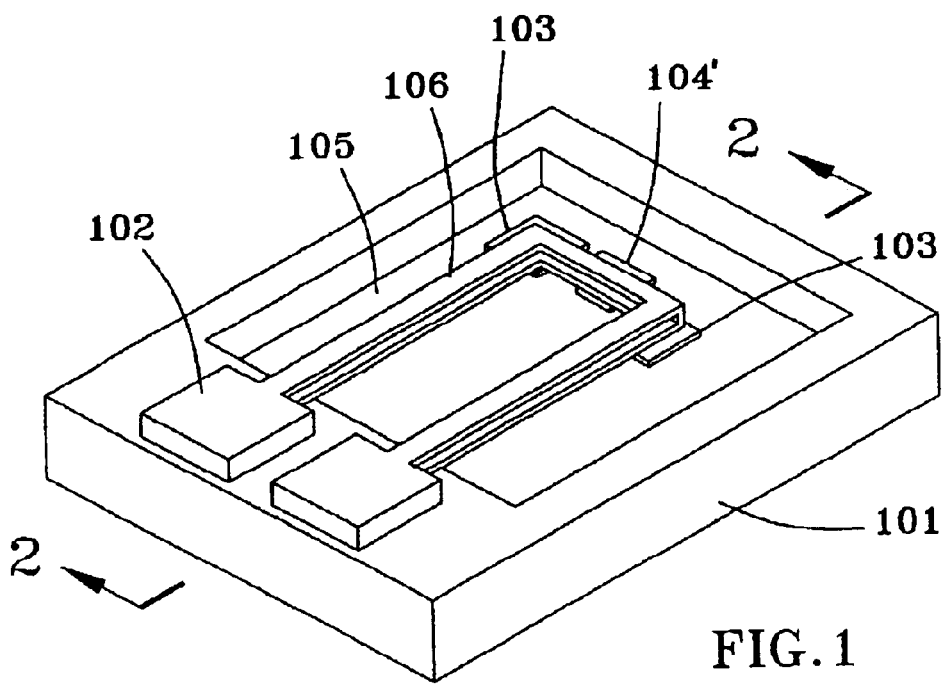
FIG. 1 is a top view of micromachined fluidic apparatus according to the invention.
Figure 2:
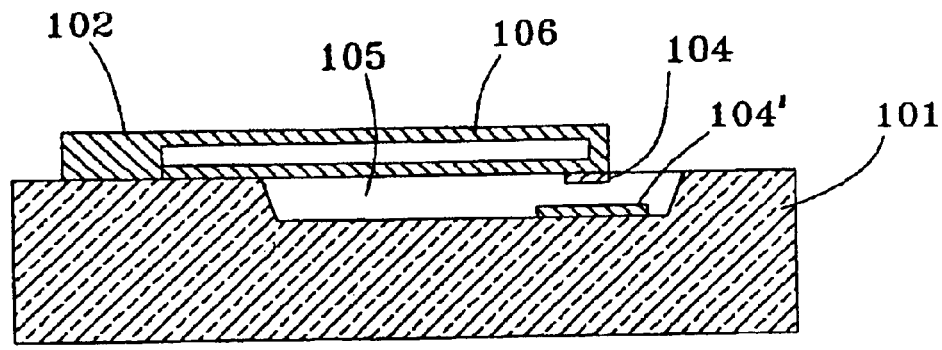
FIG. 2 is a cross section A—A of the fluidic apparatus of FIG. 1.

FIGS. 1 and 2 depict micromachined fluidic apparatus according to the invention. The system includes a substrate 101 to which there is attached a micromachined tube system 102. In the embodiment shown, a portion of the tube system 102 is attached to the top surface of the substrate 101 while the rest of the tube system is suspended above the substrate, as shown, thereby creating a free-standing tube section 106.

The substrate 101 may be an electrical insulator, conductor, or a conductor with an insulating layer. For example, the substrate may be glass (e.g., Corning 7740), ceramic, plastic, metal, alloy, silicon, or silicon with a layer of silicon oxide or silicon nitride on top. The tube system 102 may be attached to the substrate using a variety of techniques, including, but not limited to, anodic bonding, fusion bonding, eutectic bonding, thermal bonding, glass frit bonding, compression bonding, and thermal compression bonding. Note there is a gap 105 between the free-standing portion of the tube 106 and the substrate 101. This gap 105 may be created in the tube, in the substrate, or both.

The apparatus of FIGS. 1 and 2 may be used for different applications including, but not limited to, fluid flow rate measurement, fluid density measurement, fluid viscosity measurement, mixing channels, fluidic circuits, fluidic paths (tubes) and for fluidic delivery applications. In a specific example, the free-standing portion of the tube may be resonated (or vibrated) for measurement purposes, such as flow and fluid density measurements. The tube may be resonated/vibrated using many different techniques, including, but not limited to, electrostatic force (capacitive force), electromagnetic force, thermally-based actuation force (such as bimorph, shape memory alloy, and thermopneumatic), and piezoelectric force.

Elements for sensing, actuation, or both can be added as either an integrated or discrete part of the overall fluidic apparatus. The capacitive (electrostatic) actuation method for resonating the tube is the preferred choice for many applications since the two capacitive plates may be an integrated part of the overall apparatus. As shown in FIGS. 1 and 2, one plate 104 may be located on the micromachined tube, with the other plate 104' being located on the substrate.

The movement and the variations in the tube vibration may be detected via different methods, including, but not limited to, capacitive, piezoresistive, resistive, piezoelectric, magnetic, optical, and laser based techniques. Most of these detection methods may be implemented as an integral part of the overall apparatus. The capacitive detection method is the preferred method for many applications since the two capacitive plates 103 shown in FIG. 1 may be an integrated part of the overall apparatus where one plate is on the micromachined tube (not visible), and one on the substrate.

Figure 3:
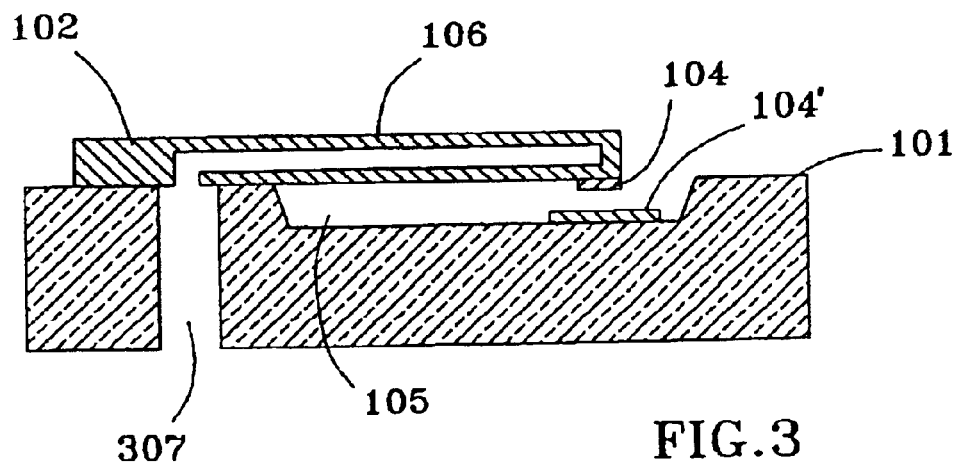
FIG. 3 is a cross section of a micromachined fluidic apparatus with inlet and outlet flow ports on the backside of the substrate via through holes in the substrate.

The flow inlet and flow outlet ports associated with the tube system may also be realized in various ways. For example, the flow ports may be on the bottom surface of the substrate, with access to the tube(s) being via through holes 307 and 407 in the substrate, as shown in FIGS. 3 and 4, respectively. These ports can also be on the top surface of the substrate, either on the substrate only, or a part of the tube may be attached on the substrate.

For many applications, a resonating tube must be packaged either in vacuum or in a pressure controlled environment in order to achieve a high resonant frequency and a high Q-factor. As shown in FIG. 4, the fluidic apparatus may be packaged by hermetically attaching a cap 408 to the device substrate 401. Such attachment may be performed in vacuum, or in a controlled environment to realize a desired level of evacuation. Additionally or instead, a getter material of a type known in the art can be sealed within the hermetically-sealed enclosure formed between the cap 408 and substrate 401 to produce or maintain a vacuum or other controlled environment within the enclosure.

Electrical lead transfer from within the cap 408 to the outside may be achieved in different ways. For example, from backside of the substrate using through holes 409 in the substrate 401, or lead transfer lines 410 may be disposed on the front side of the substrate. The cap 408 may be made from a variety of materials, including but not limited to glass, ceramic, plastic, metal, silicon, and silicon with a layer of silicon dioxide, or silicon nitride, or both.

An integrated-circuit chip may be added to the fluid apparatus in many different ways, including, but not limited to, placement of the chip on the top surface of the substrate (either inside the cap or outside), or on the bottom surface of the substrate, in the same package as the sensor chip (i.e. hybrid packages). Additional micromachined tube system(s) may also be attached to either side of the substrate, as shown in FIG. 5. Bottom-mounted tube systems may be completely attached or may have free-standing parts. One tube system may also be connected to another, as through conduit 502.

In alternative embodiments, micro-fluidic systems according to the invention may be stacked to facilitate more complex three-dimensional fluidic channels and circuits. With these approaches, flow may be routed, switched, branched and/or measured through different channels. Stacked fluidic concepts of this kind may also facilitate process integration because sensing elements flow sensors, actuating elements, micropumps, flow switches or valves and other devices may be fabricated separately and joined together into a single package.

Theory and Operation of Coriolis Mass Flowmeters

A specific implementation of the fluidic apparatus disclosed is a Coriolis-force-based flow sensing apparatus. The theory and operation of such a flow sensor will first be described, followed by a description of a micromachined version of the flow sensing system.

Coriolis force, also known as gyroscopic force, is generally associated with a continually rotating system. This force is most famous for the effects of the earth's rotation, for example, causing winds from a high-pressure area to spiral outward in a clockwise direction in the northern hemisphere and counter-clockwise in the southern hemisphere. Other familiar examples of Coriolis force effects include: (i) projectiles fired from a gun in the northern hemisphere appear to veer slightly to the right, while in the southern hemisphere they appear to veer to the left; and (ii) a body moving on a rotating frame of a reference, such as a merry-go-round, experiences a lateral force and must lean sideways in order to move forward when walking outward along the radius. Coriolis force is the result of the Newton's equation (F=ma) in a rotating reference frame.

The magnitude of this force is very small, and can be calculated from the equation:

$$F_C = 2m\omega \times V \quad (1)$$

where, $F_C$ designates the Coriolis force (vector), m is mass, $\omega$ is the angular velocity of the rotation axis (vector), x is the vector cross product operation, and V is the particle velocity (vector) relative to the rotation axis. Note that the force ($F_C$) does indeed arise from the motion of the particle. Since the force ($F_C$) is proportional to V, it vanishes if there is no particle motion (flow).

Figure 6A:
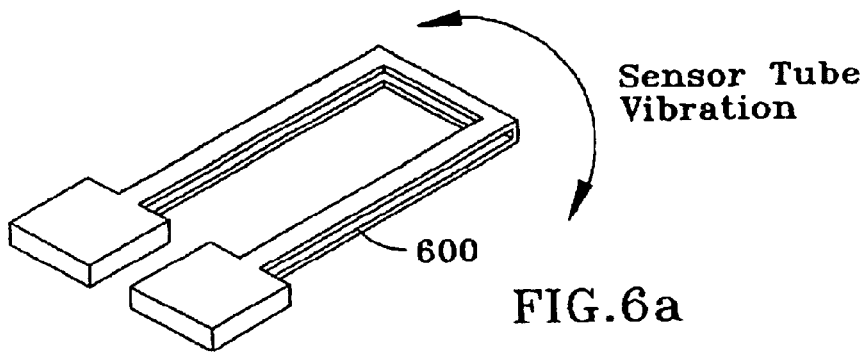
FIG. 6A is a drawing of a Coriolis-force-based flow sensor according to the invention.
Figure 6B:
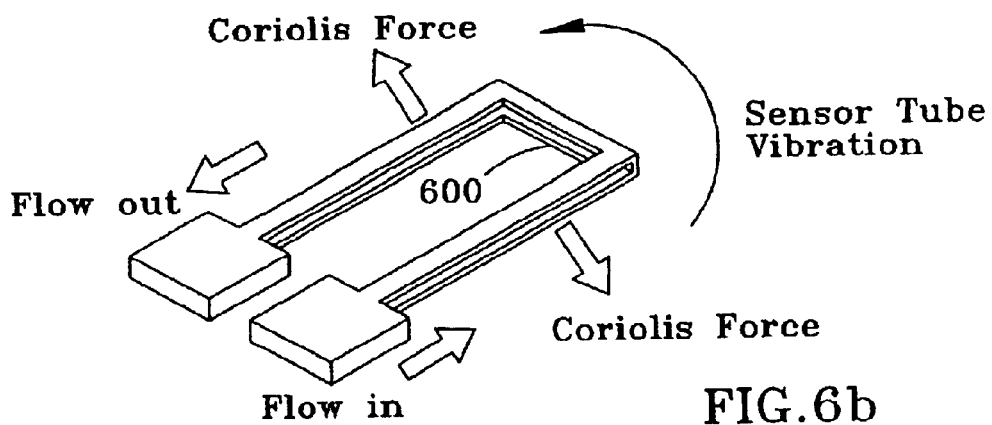
FIG. 6B illustrates, from an oblique perspective, the basic operation of the Coriolis-force-based sensor of FIG. 6A.
Figure 6C:
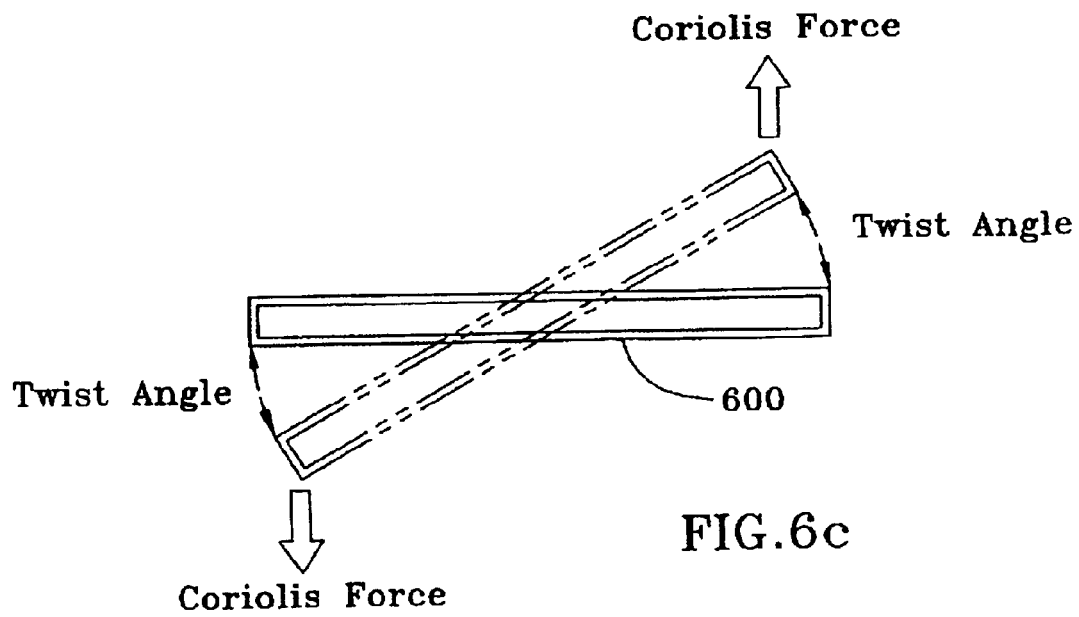
FIG. 6C is a side-view drawing better illustrating the way in which a microtube according to the invention twists in accordance with Coriolis flow.

FIGS. 6A–6C depict the basic operation of a mass flow meter using Coriolis force principles. Inside the flow meter housing is a U-shaped tube 600 which vibrates vertically at its resonant frequency (FIG. 6A). The flow tube 600 is usually driven by an electromagnetic driving coil located at the center of the bend in the tube (not shown). Due to the tube's upward momentum as the fluid travels around the tube bend, the fluid flowing out of the sensor resists having its vertical motion decreased by pushing up on the tube (FIG. 6B). The resulting force causes the flow tube to twist (FIG. 6C). When the tube is moving downward during the second half of its vibration cycle, it twists in the opposite direction. This twisting characteristic is referred to as the Coriolis effect.

Figure 7A:
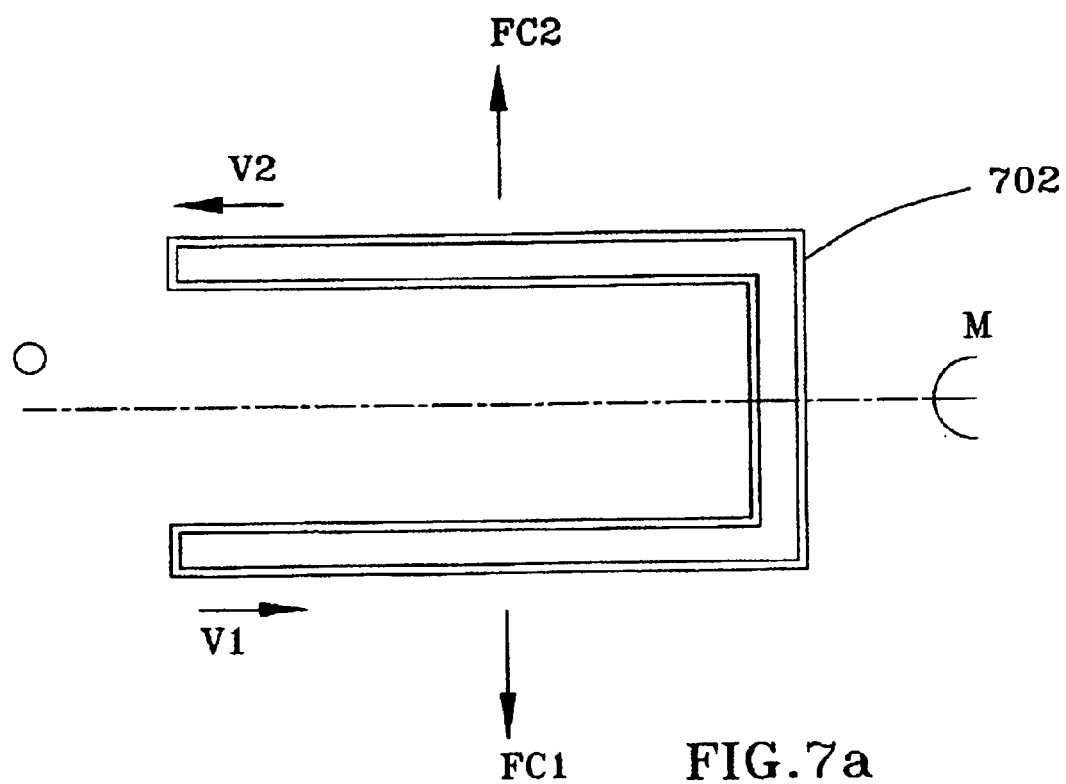
FIG. 7A shows the operation of a Coriolis tube.
Figure 7B:
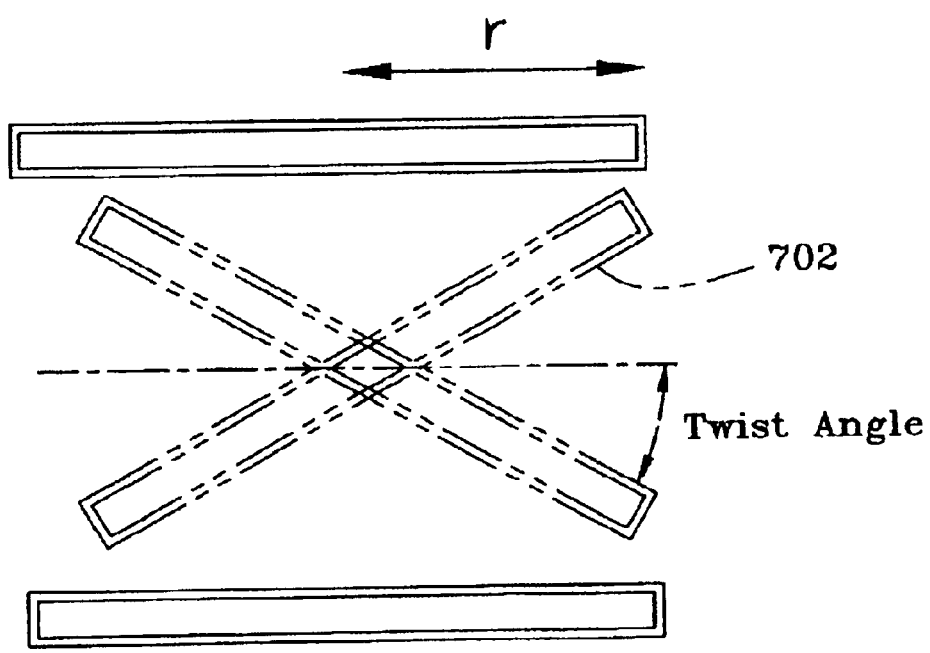
FIG. 7B is a side view of the tube twisting motion.

FIGS. 7A and 7B illustrate a U-shape tube 702, showing both the axis of oscillation ($\omega$) and a unit length of fluid in each leg of the tube. As can be seen, the flow velocity vectors ($V_1$ and $V_2$) are perpendicular to the angular-rotation vector $\omega$; the force vectors ($F_{C1}$ and $F_{C2}$) are opposite to each other, due to the fact that the flow velocity vectors are in opposite directions. Likewise, in the operation of a flowmeter, its microtube vibrates with an angular velocity $\omega$, a sinusoidal function (as with a tuning fork). Consequently, the generated Coriolis forces, $F_{C1}$ and $F_{C2}$, are also sinusoidal and 180° out of phase with each other. These two Coriolis forces, $F_{C1}$ and $F_{C2}$, result in an oscillating moment M about axis "O" as shown in FIG. 7(a). The incremental moment ($\Delta M$) can be derived, as follows $$\Delta M = F_{C1}r_1 + F_{C2}r_2 \quad (2)$$

If the selected geometry is symmetric, the two terms then become the same (simply $F_{C1}=F_{C2}=F_C$, and $r_1=r_2=r$). The calculation for the incremental moment may then be simplified to:

$$\Delta M = 2F_C r = 4m|\omega \times V|r \quad (3)$$

by substituting for $F_C$ from equation (1). $\Delta M$ can also be expressed as a function of the incremental mass flow rate ($\Delta q$)

$$\Delta M = 4\omega r L q \quad (4)$$

The total moment, M, about axis "O" due to Coriolis force on all moving particles is given by:

$$\Delta M = 4\omega r L q \quad (5)$$

where q is the mass flow rate in the U-shape tube, and L is the tube length which is perpendicular to tube vibrating axes. The moment, M, due to Coriolis force, causes an angular deflection of the U-shape tube about the central axis. The angular deflection can be seen from the side view of FIG. 7B, which shows the resultant twisting motion.

The torque for any given tube can be determined by:

$$\text{Torque} = K_s \partial \quad (6)$$

where $\partial$ is the twisting angle of the tube, and $K_S$ is the angular spring constant of the tube. Using this equation, we can relate the mass flow rate q to the deflection angle as follows:

$$q = K_S \partial / (4\omega L r) \quad (7)$$

Thus, the mass flow rate q is directly proportional to the deflection angle $\partial$, and inversely proportional to the angular velocity $\omega$ of the tube. For a given tube geometry and material composition, mass flow may be determined by measuring the resonant frequency and the twisting angle. There are several ways of detecting the twisting angle (angular motion) such as optical, piezoresistive, and capacitive. A capacitive technique is preferred according to the invention due to its simplicity and accuracy.

The vibrating U-tube method of measurement also produces an output, which is proportional to the density of the fluid in the meter. The natural frequency (f) of a spring system can be calculated directly from the mass (m) and the spring constant (k) as, $$F = k[1/m]^{1/2} \quad (8)$$

In the case of the flow tube, the vibrating system may be divided into the tube mass ($m_t$) and the fluid mass ($m_f = \rho V$). The fluid mass in turn is proportional to the fluid density ($\rho$) since the tube volume (V) is constant. Therefore the density can be expressed directly in terms of the tube frequency (f) as, $$\omega = 2\pi f = [K/(m_t + \rho V)]^{1/2} \quad (9)$$

$$\rho = 1/V[(K/4\pi^2 f^2) - m_t] \quad (10)$$

Thus, by measuring the resonant frequencies with two different known fluids of known density (at the same temperature); this method may be used to measure the density of any unknown fluid.

A Micromachined Coriolis-Force-Based Flow Sensing Apparatus

The micromachined fluidic apparatus described with reference to FIGS. 1–5 may be used in conjunction with a Coriolis-force-based flow sensing system. By way of review, such apparatus comprises: (i) a micromachined tube system, (ii) substrate with top and bottom surfaces, (iii) where part of the tube is attached to the top surface (or bottom) of the substrate, while the rest of the tube is free-standing with respect to the substrate, and (iv) flow inlet and outlet ports where gas or liquid can flow through the tube system.

According to this particular embodiment of the invention, the tube is resonated, and the twist in the tube as a result of flow and its associated Coriolis force is measured in order to detect the mass flow rate of the gas or liquid. The resonant frequency of the tube is then monitored to measure the density of the gas or liquid. The apparatus depicted in FIGS. 1 and 2 represent a preferred implementation of a Coriolis force base flow sensor according to the invention. In this configuration, the free-standing part of the tube 106 is electrostatically resonated via two capacitive plates, one (104) on the middle of the tube 106, and one (104') located on the substrate 101 with a face-to-face overlap therebetween. Four capacitive plates 103 and 103' are preferably used to measure the twist of the tube 106 (103'); two on the corners of the tube 6, and the other two facing them on the substrate 101 (103).

If the tube is constructed from an electrically conductive material (e.g., silicon), then the resonating tube and the two measurement plates on the tube can be replaced by the conductive body of the tube itself. A cap may be used for packaging in vacuum or a controlled-pressure environment. As shown in FIG. 4, the electrical lead transfers 409 may be made from bottom surface of the substrate via through holes in the substrate; or lead transfers 410 can be implemented via metal lines on the top surface of the substrate, as well. A custom-designed electronics chip can be added to the flow Coriolis-force-based sensor in various ways, as discussed previously. In addition, the electronic chip may function as both the actuation source at the resonant frequency, as well as for measuring the variation in the capacitance due to flow and/or the change in the resonant frequency when the tubes are filled with fluids.

Figure 8A:
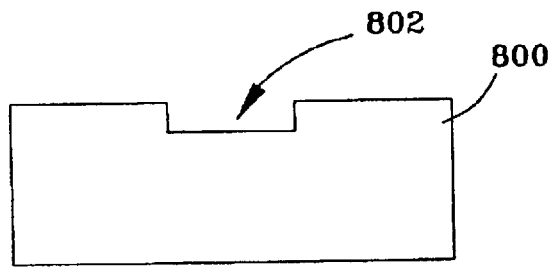
FIGS. 8A–8G illustrate a fusion-bonding-based fabrication process flow to create micromachined tubes and a fluidic apparatus according to the invention.
Figure 8B:
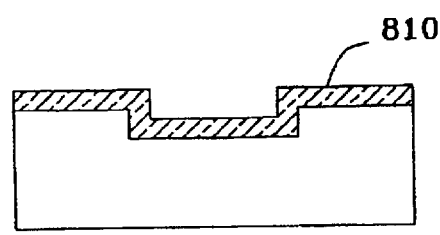

Fabrication of Micromachined Tubes using Fusion Bonding Techniques and Implementation of the Fluidic Apparatus One approach to fabricate micromachined tube systems of the type described herein is through the use of fusion-bonding techniques. FIGS. 8A–8G show a simplified fabrication process flow to fabricate such micromachined tubes and the fluidic apparatus. In one possible approach, two silicon wafers 800 and 820, and a glass wafer 840 are used. First a tube cavity 802 is created in the first silicon wafer, either by dry or wet etching (FIG. 8A). This is followed by a first boron diffusion step (810) to create the tube body (FIG. 8B). A second boron doped layer 830 is formed in the second silicon wafer (820), which can be flat or include a corresponding tube cavity. The two wafers may be polished (an optional step) in order to provide very polished and smooth surfaces.

Figure 8C:
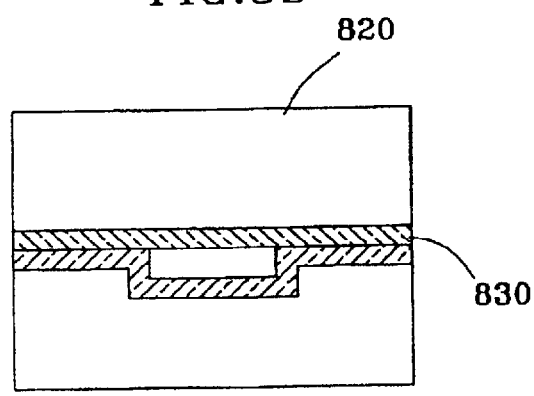
Figure 8D:
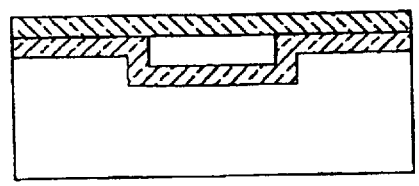
Figure 8E:
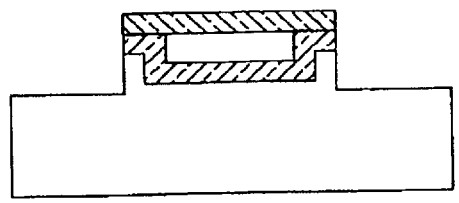

The two silicon wafers are then attached together via fusion bonding (or other bonding techniques such as eutectic bonding, anodic bonding, thermal bonding, adhesive bonding etc.), as shown in FIG. 8C. It is possible to use an intermediate layer (e.g. silicon dioxide, silicon nitride, sputtered glass, or metals) on one or both the silicon wafers before bonding them together. The backside of the first silicon wafer 800 is protected, and the bonded wafers are then etched in a selective silicon etchant (such as EDP) which etches the undoped silicon and stops at the boron doped silicon (see FIG. 8D). Now the tube is patterned and etched, using either dry or wet etching techniques, as shown in FIG. 8E. Tube formation may also be performed at other steps. For example, the tube may be formed with the same etching step that defined the tube cavity in FIG. 8A.

Figure 8F:
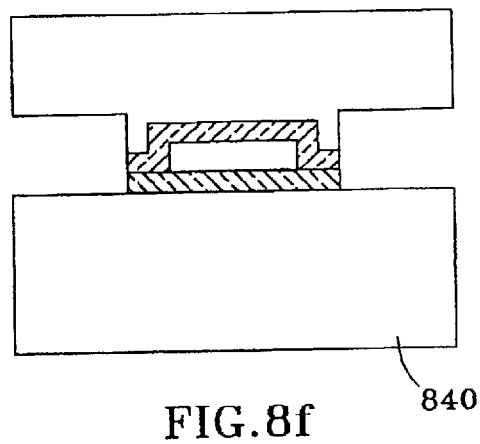
Figure 8G:
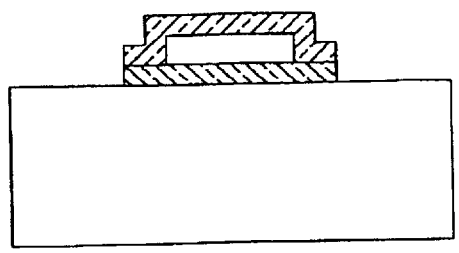

The silicon wafer is attached to a substrate; for example it is anodically bonded to a glass wafer 840 (FIG. 8F). The protection layer on the backside of the first silicon wafer is removed. Again, the glass and silicon wafer is etched in a selective silicon etchant (such as EDP). Now the fluidic apparatus is formed, as shown in FIG. 8G.

Possible options to the process just described include (1) depositing and patterning metal layers on silicon, glass or both, (2) creating a gap between the resonating tube and the glass substrate in glass, silicon or both, (3) adding a cap for packaging in vacuum or controlled pressure environments, (4) input/output flow ports can be created in the glass or silicon or both, and (5) electrical lead transfers can be created either from top surface of the glass substrate, or from the backside of the glass substrate via through holes in it.

These various approaches may be implemented in different ways. For example, instead of using the technique of selective etching of boron-doped versus undoped silicon, one can use the technique of selective etching of p-type versus n-type silicon in an electrochemical-based approach. Another selective etching technique involves using silicon-on-insulator (SOI) wafers. Here, the buried silicon oxide layers are used as an etch stop, either for wet or dry etching techniques. It is also possible to have one or more layers of interface material (for example silicon dioxide) on one or both of the silicon wafers and perform the fusion bonding on these interface material.

Figure 9A:
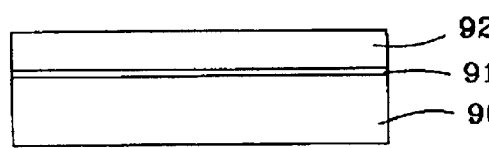
FIGS. 9A–9G illustrate a fusion-bonding-based fabrication process flow using silicon-on-insulator (SOI) and/or epitaxial silicon wafers.
Figure 9B:
Figure 9C:
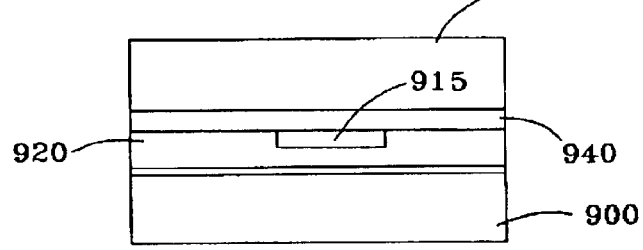
Figure 9D:
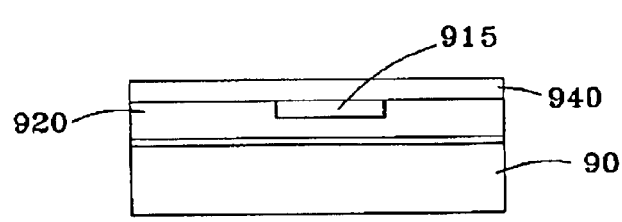
Figure 9E:
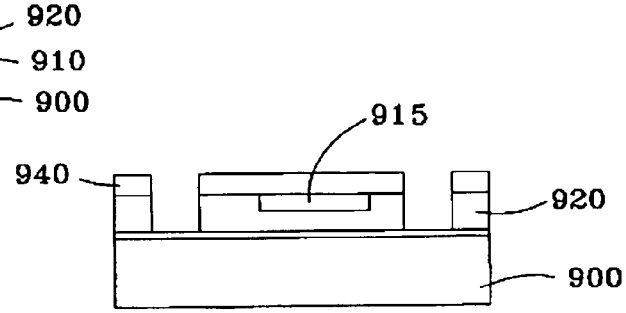
Figure 9F:
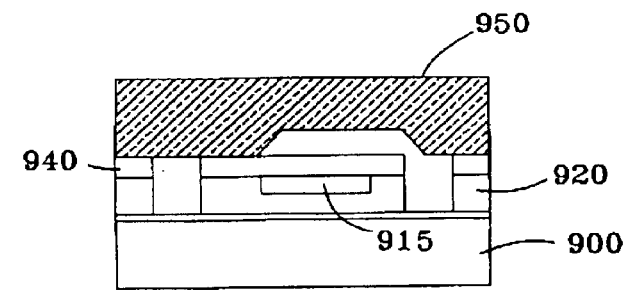
Figure 9G:
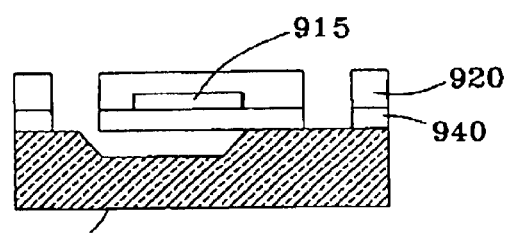

FIGS. 9A–9G show a simplified fabrication process flow used to fabricate micromachined tubes and the fluidic apparatus using a silicon-on insulator wafer, an epitaxial silicon wafer and a glass wafer. FIG. 9A shows a silicon-on-insulator wafer (910 on 900). A tube cavity 915 is created in a first structural layer 920 of the SOI wafer (FIG. 9B), using either dry or wet etching. This is followed by fusion bonding of this wafer to an epitaxial wafer 930 as shown in FIG. 9C. The supportive layer 900 of the SOI wafer is protected, and the bonded wafers are then etched in a selective silicon etchant (such as EDP) which etches the undoped silicon and stops at the boron doped second structural layer 940 of the epitaxial silicon wafer (see FIG. 9D). Now the tube is patterned and etched, using either dry or wet etching techniques (FIG. 9E). The silicon wafer is then attached to a substrate; for example, it may be anodically or otherwise bonded to a glass wafer 950, as shown in FIG. 9F. The protection layer on the backside of the first silicon wafer is removed. Again, the glass and silicon wafer is etched in a selective silicon etchant (such as EDP) so as to terminate on the oxide layer, thereby forming microtubes, as shown in FIG. 9G.

Possible options to the process just described include (1) depositing and patterning metal layers on silicon, glass or both, (2) creating a gap between the resonating tube and the glass substrate in glass, silicon or both, (3) adding a cap for packaging in vacuum or controlled pressure environments, (4) input/output flow ports can be created in the glass or silicon or both, (5) electrical lead transfers can be created either from top surface of the glass substrate, or from the backside of the glass substrate via through holes in it, and (6) the second epitaxial wafer can be replaced by (i) an Silicon-on-Insulator (SOI) wafer, (ii) a wafer with a boron doped layer, and (iii) other approaches allowing selective etching.

Figure 10A:
FIGS. 10A–10K illustrate a chevron-shape-based fabrication process flow to create micromachined tubes and the fluidic apparatus.
Figure 10B:
Figure 10C:
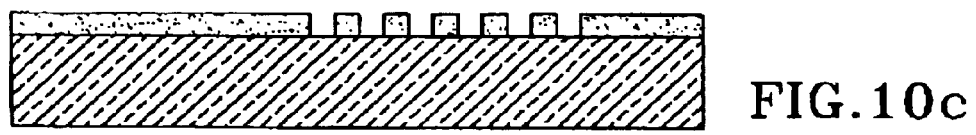
Figure 10D:
Figure 10E:
Figure 10F:
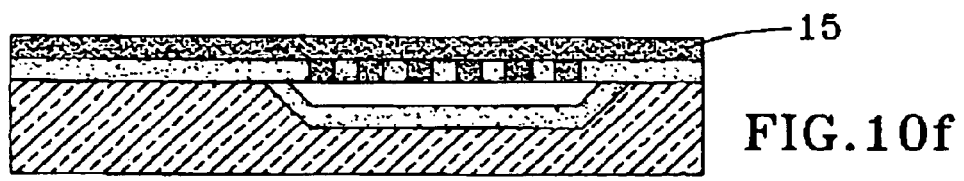
Figure 10G:
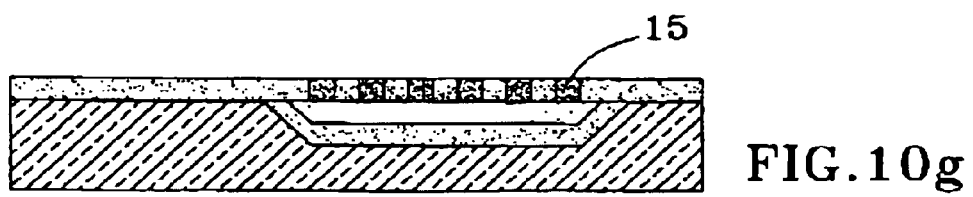

Fabrication of Free-Standing Micromachined Tubes using Chevron-Shape Opening Techniques and Implementation of the Fluidic Apparatus According to an alternative method of the invention, one silicon wafer is used for the formation of the tube system, including the free-standing and stationary microtube sections. This wafer is then attached to a substrate, for example anodically bonded to a glass wafer. FIGS. 10A–10K illustrate a sequence of steps applicable to the method. Beginning with a base layer 11 (for example, a silicon wafer), a structural material 13 (for example boron-doped silicon) is first formed atop of the base substrate 11 (FIG. 10B). A chevron shaped pattern, an example of which is shown in FIGS. 11A & 11C, is etched and penetrated into the structural material 13 using a dry etch technique (such as plasma, RIE, or deep RIE), see FIG. 10C.

Via these chevron-shape openings, the base layer under the chevron patterns is then etched in a wet or dry etchant, which selectively etches the substrate beneath the structural material 13. Thus, the etching process selectively etches off the base layer under layer 13 to a pre-determined depth (FIG. 10D), thereby creating the tube cavity. Additional structural material 14 is then formed within the etch channels under the chevron patterns, as shown in FIG. 10E. One approach to create such additional structural material 14 inside the tube is by performing a boron diffusion process step. The chevron-shape openings allow the carrier gas to transfer boron atoms (or other material) inside the tube cavity. Therefore, the formation of the additional structural material occurs from within the tube cavity via the chevron-shape openings.

The chevron opening is then sealed with another structural materials (15). This may be achieved, for example, by depositing one or more layers (e.g. LPCVD Silicon dioxide, silicon nitride and polysilicon), as shown in FIG. 10F. Optionally, as illustrated in FIG. 10G, the layer 15 can then be removed except in the etched area. This removal may be done via a maskless plasma etch. For example, the sealing material 15 can consist of (1) an etch stop layer made from LPCVD oxide, and (2) a filling material from LPCVD polysilicon. A dry etch back is performed until the etch reaches the etch stop layer. A repeat process of the fillings and etch back may be necessary to ensure that the microchannels are hermetically sealed.

Figure 10H:
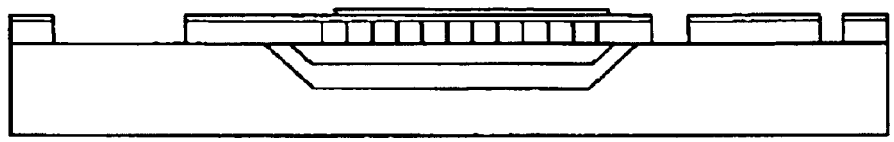
Figure 11A:
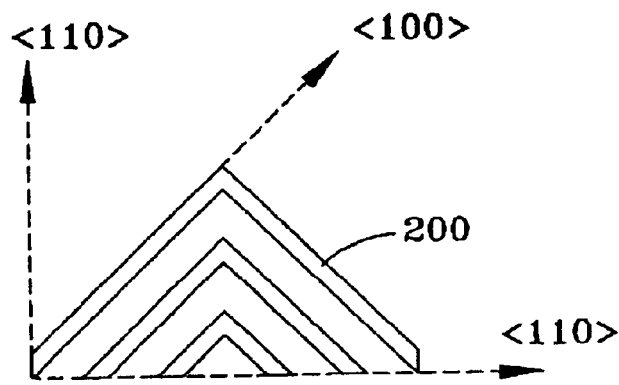
FIGS. 11A–11C shows different perspectives associated with a chevron shaped pattern according to the invention.
Figure 11B:
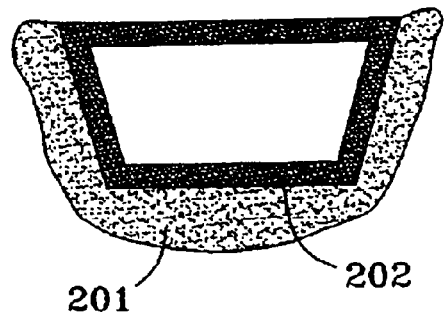
Figure 11C:
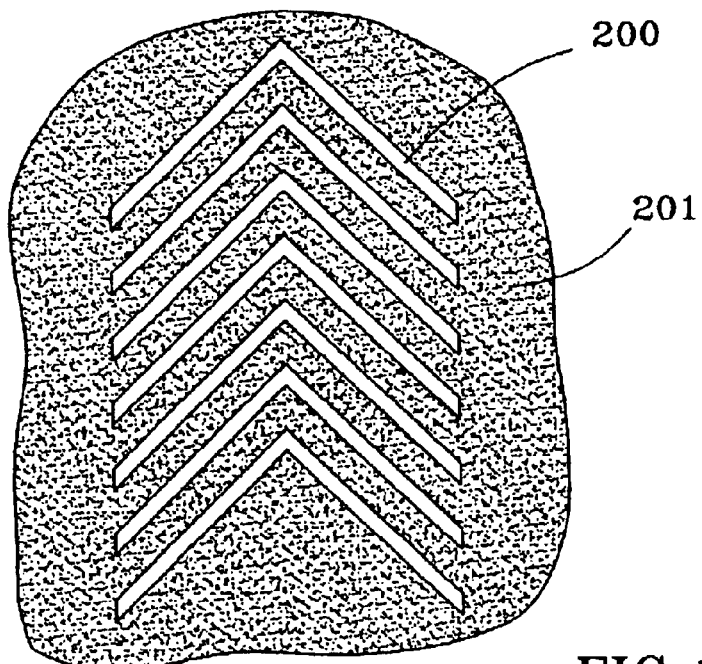

To define the micro-fluidic device, layer 13 and 14 atop base layer 11 is then patterned and etched (either wet or dry), as shown in FIG. 10H. The etch depth is preferably greater than the thickness of 13 to make certain that the support layer 11 underneath is exposed.

Figure 10I:
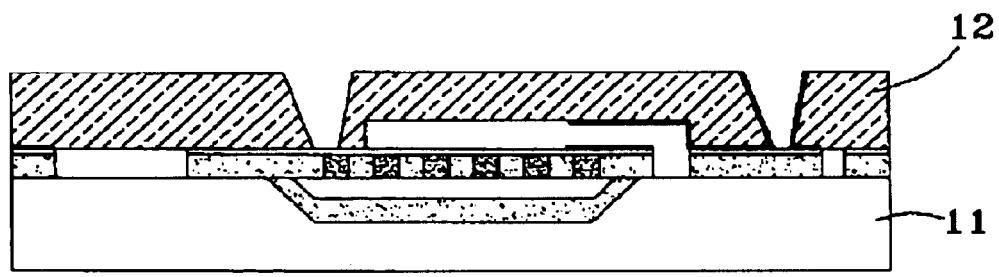

Referring to FIG. 10I, the supportive layer 11 with micro-fluidic structures and/or sensing electrodes thereon is then attached to a housing substrate 12. A variety of substrates (including but not limited to glass, silicon, silicon with a layer of dielectric, and ceramic) and attachment techniques can be used (including but not limited to anodic bonding, fusion bonding, eutectic bonding, thermal bonding, glass frit bonding, compression bonding, and thermal compression bonding). A preferred method is anodically bonding a silicon support substrate 11/13 to a glass wafer housing substrate 12.

Figure 10J:
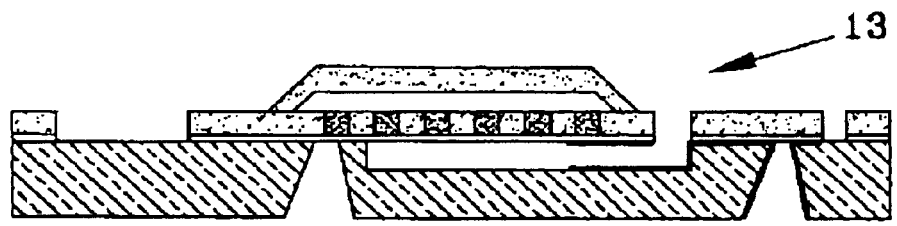
Figure 10K:
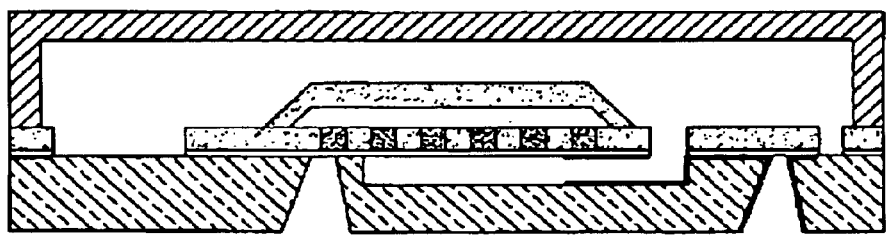

After the attachment to the housing substrate (FIG. 10I), the support substrate 11 is selectively removed while the tube system 13 remains (FIG. 10J). As a result, the fluidic system is now created on top of the housing substrate 12 through the attachment process followed by removing layer 11. Various types of etchants, such as ethylene diamine pyrocatechol (EDP), KOH, or TMAH may be used to selectively etch away the supportive substrate 11 (for example, an undoped silicon substrate) and the etch stops at the structure layer 13, (for example, heavily boron doped silicon). Other selective etching techniques include (but not limited to) electrochemical etching of n-type and p-type silicon, and using SOI wafers by etch stopping at the insulator layer.

Possible options here include (1) depositing and patterning metal layers on silicon, glass or both as shown in FIG. 10J, (2) creating a gap between the resonating tube and the glass substrate in glass, silicon or both (FIG. 10J), (3) adding a cap for packaging in vacuum or controlled pressure environments (FIG. 10K), (4) creating input/output flow ports in the glass or silicon or both, and (5) creating electrical lead transfers, either from top surface of the housing substrate 12, or from the backside of the housing substrate via through holes.

We claim:

1. A method of fabricating a micromachined tube for fluid flow, comprising the steps of:

etching a recess in a surface of a first material;
enclosing the recess with a second material to define a tube cavity; and
defining an exterior of the tube by removing at least portions of at least one of the first and second materials, wherein at least one of the first and second materials is a substrate, the tube is on or within the substrate and has a length between a fluid inlet and a fluid outlet port, and a section of the tube is free-standing relative to the substrate as a result of the step of defining the exterior of the tube.

2. The method of claim 1, wherein the first, second, or both materials comprise a doped or undoped silicon wafer with or without an epitaxial layer, or a polished silicon-on-insulator (SOI) substrate.

3. The method of claim 1, wherein the recess is enclosed by joining the first and second materials using anodic bonding, silicon fusion bonding, adhesive bonding, eutectic bonding, thermal compression bonding, compression bonding, or a combination thereof.

4. The method of claim 1, wherein the second material comprises a doped region and an undoped region, and the recess is enclosed by bonding the doped region of the second material to the first material.

5. The method of claim 4, wherein the exterior of the tube is defined by completely removing the undoped region of the second material so that the doped region of the second material defines a portion of the exterior of the tube.

6. The method of claim 5, wherein the exterior of the tube is further defined by removing portions of the doped region of the second material and portions of the first material.

7. The method of claim 5, further comprising the steps of bonding the exterior of the tube to a third material so that the tube is between the first and third materials, and then completely removing an undoped region of the first material.

8. The method of claim 1, further comprising the step of doping the surface of the first material in which the recess was etched to define a doped region overlying an undoped region, the recess being enclosed by bonding the doped region of the first material to the second material, and the doped region of the first material defining a portion of the exterior of the tube following the removing step.

9. The method of claim 1, wherein the first material is a layer on a silicon-on-insulator substrate and the recess is etched in the layer.

10. A method of fabricating a micromachined free-standing tube, comprising the steps of:

defining a plurality of closely spaced slit openings in a first material;
undercutting a plurality of the slit openings to form a continuous channel beneath and connected to the openings; and
enclosing the channel by sealing the slit openings with a second material to form a tube with a continuous tube cavity beneath the first and second materials.

11. The method of claim 10, wherein the first material overlies a substrate and the channel is formed in the substrate during the undercutting step.

12. The method of claim 10, wherein the slit openings are chevron-shaped.

13. The method of claim 11, further comprising the step of removing portions of the substrate so that a section of the tube is free-standing relative to the substrate.

14. The method of claim 11, wherein the step of undercutting the plurality of the slit openings is an etching step that selectively etches a contiguous portion of the substrate beneath the first material and the slit openings.

15. The method of claim 11, further comprising the steps of bonding a second substrate to the first material so as to enclose the tube between the second substrate and the substrate in which the channel was formed, removing the substrate in which the channel was formed, and then bonding a cap to the second substrate so as to enclose the tube between the second substrate and the cap.

16. A method of fabricating a micromachined tube for fluid flow, the method comprising the steps of:

etching a recess in a surface of a first material;

enclosing the recess with a second material to define a tube cavity; and defining an exterior of the tube by removing at least portions of at least one of the first and second materials;

wherein the first material is a layer on a silicon-on-insulator substrate and the recess is etched in the layer; and wherein the second material comprises a doped region and an undoped region, end the recess is enclosed by bonding the doped region of the second material to the layer of the first material.

17. The method of claim 16, wherein a portion of the exterior of the tube is defined by completely removing the undoped region of the second material.

18. The method of claim 17, wherein a portion of the exterior of the tube is further defined by removing portions of the doped region of the second material and portions of the layer of the first material.

19. The method of claim 18, further comprising the steps of bonding the doped region of the second material to a third material so that the tube is between the third material and the silicon-on-insulator substrate, and then removing the silicon-on-insulator substrate.

* * * * *